United States Patent [19]

Innes

[11] Patent Number: 4,532,244

[45] Date of Patent: Jul. 30, 1985

[54] METHOD OF TREATING MIGRAINE HEADACHES

[76] Inventor: Margaret N. Innes, 5558 SW. Anhinga Ave., Palm City, Fla. 33490

[21] Appl. No.: 647,686

[22] Filed: Sep. 6, 1984

[51] Int. Cl.³ .............................................. A61K 31/46
[52] U.S. Cl. .................................... 514/291; 514/953; 514/964
[58] Field of Search ............................................ 424/265

[56] References Cited

U.S. PATENT DOCUMENTS

| | | | |
|---|---|---|---|
| 2,276,677 | 3/1942 | Vollmer | 167/67 |
| 3,865,933 | 2/1975 | Mudge | 424/153 |
| 3,888,975 | 6/1975 | Ramwell | 424/15 |
| 3,993,057 | 11/1976 | Ramwell | 128/130 |
| 4,026,290 | 5/1977 | Brooker et al. | 128/260 |
| 4,070,463 | 1/1978 | Graybiel | 424/247 |
| 4,201,211 | 5/1980 | Chandrasekaran et al. | 128/268 |
| 4,369,172 | 1/1983 | Schor et al. | 424/19 |
| 4,389,393 | 6/1983 | Schor et al. | 424/19 |

OTHER PUBLICATIONS

Chem. Abst., 69, (1968)–1712v.
Chem. Abst., 92, (1980)–34168a.
Stedman's Medical Dictionary, 24th Ed., 1982, p. 879.
Merck Manual, 1982, pp. 1299–1300.
Goodman et al.: The Pharmacological Basis of Therapeutics, 5th Ed., 1975, pp. 877–878.
Rengstorff et al.: "Mydriatic and Cycloplegic Drugs: A Review of Ocular and Systemic Complications", J. Optom. Physiol. Opt., 1982 Feb., 59(2), pp. 162–177.
Behbehani, "The Role of Acetylcholine in the Function of the Nucleus Raphe Magnus and In . . . ", Brain-Res., 1982 Dec. 9, 252(2), pp. 299–307.
Briggs, et al.: "Effect of Preanaesthetic Medication on Anaesthesia with ICI 35, 868", Br. J. Anaesth., 1982 Mar., 54(3), pp. 303–306.
Sitaram et al.: "Development and Use of Pharmacological Probes of the CNS in Man: . . . ", Biol. Psychiatry., 1980 Dec., 15(6), pp. 925–955.
Dykstra, "Discrimination of Electric Shock: Effects of Some Opioid and Non-Opioid Drugs", J. Pharmacol. Exp. Ther., 1980 May, 213(2), pp. 234–240.
Longo et al.: "Results of a Randomized Double-Blind Crossover Trial of Scopolamine Versus Placebo . . . ", Cancer. Treat. Rep., 1982 Nov., 66(11), pp. 1975–1976.
Arnt et al.: "Differential Reversal by Scopolamine of Effects of Neuroleptics in Rats. Relevance . . . ", Neuropharmacology, 1981 Dec., 20(12B), pp. 1331–1334.
"Transdermal Scopolamine for Motion Sickness", Med. Lett. Drugs. Ther., 1981, Oct. 16, 23(21), pp. 89–90.
Laitinen et al.: "Scopolamine Alone or Combined with Ephedrine in Seasickness: A Double-Blind, Placebo–Controlled Study", Aviat. Space. Environ. Med., 1981 Jan., 52(1), pp. 6–10.
Price et al.: "Transdermal Scopolamine in the Prevention of Motion Sickness at Sea", Clin. Pharmacol. Ther., 1981 Mar., 29(3), pp. 414–419.
McCauley et al.: "Effect of Transdermally Administered Scopolamine in Preventing Motion Sickness", Aviat. Space. Environ. Med., 1979 Nov., 50(11), pp. 1108–1111.

Primary Examiner—Stanley J. Friedman
Attorney, Agent, or Firm—Cushman, Darby & Cushman

[57] ABSTRACT

Migraine headaches are treated or prevented by the administration of scopolamine or a pharmaceutically acceptable salt thereof. Preferably scopolamine hydrocloride is administered to the patient transdermally at a substantially constant rate using a metered drug delivery system conveniently adhered to the patient's skin.

6 Claims, No Drawings

METHOD OF TREATING MIGRAINE HEADACHES

BACKGROUND OF THE INVENTION

This invention relates to the treatment of migraine headaches and more particularly to the use of scopolamine when administered in a transdermal therapeutic system which is programmed to deliver a measured quantity of scopolamine over a predetermined period of time.

Migraine is a paroxysmal disorder characterized by recurrent attacks of headache, with or without associated visual and gastroinestinal disturbances.

Etiology and Incidence: The cause of migraine is unknown, but evidence suggests a functional disturbance of cranial circulation. Prodromal symptoms (e.g. flashes of light, hemianopia, paresthesias), are probably due to intracerebral vasonconstriction, and the head pain to dilation of scalp arteries. Migraine may occur at any age but usually begins between ages 10 and 30, more often in women than in men. Remission after age 50 is not uncommon.

Symptoms and Signs: Headache may be preceded by a short period of depression, irritability, restlessness, or anorexia, and in some patients by scintillating scotomas, visual field defects, paresthesias, or (rarely) hemiparesis. These symptoms may disappear shortly before the headache appears or may merge with it. Pain is either unilateral or generalized. Symptoms usually follow a pattern in each patient, except that unilateral headaches may not always be on the same side. The patient may have attacks daily or only once in several months.

Untreated attacks may last for hours or days. Nausea, vomiting, and photophobia are common. The extremities are cold and cyanosed, and the patient is irritable and seeks seclusion. The scalp arteries are prominent, and their amplitude of pulsation is increased. Intracranial vascular malformations are a rare cause of migrainous headaches; other manifestations are seizures, cranial bruits, signs of a mass lesion, or subarachnoid hemmorhage.

Diagnosis is bases on the symptom patterns described above in a patient who shows no evidence of intracranial pathologic changes. The diagnosis is more probable with a family history of migraine or if visual prodromata occur. See *The Merck Manual of Diagnosis and Therapy*, fourteenth edition, 1982, p. 1299.

Previous migraine treatments have included asprin or codine to alleviate mild attacks and in severe attacks ergotamine tartrate in an amount of from 0.25 to 0.5 milligrams per dose, not to exceed 1.0 milligrams per 24 hour period, is indicated, either given by the subcutaneous, intramuscular or sublingual route of administration. Once therapy has been begun the patient is typically instructed to lie down in a quiet, dark room for at least two hours. The speed and thoroughness of the relief from pain are reported to be directly proportional to the promptness with which medication is started after the onset of an attack.

It is important, according to prior therapies, that treatment be started early, as quickly after the onset of an attack as possible. If the attack has reached its peak, larger amounts of ergotamine are required and not only is a longer time required for effective action but also unpleasant side effects from the medication are more pronounced. Depending upon the route of administration, the quantity of ergotamine administered has a definite upper limit per 24 hour period, an excess of which causes untoward, sometimes severe, side effects. While parenterally administered ergotamine may often bring prompt relief, oral medication, which is the type typically taken by a patient that is not institutionalized, requires a longer period of time to provide the degrees of relief desired, an average of 5 hours being required. Even then, according to the literature ergotamine may fail in severe attacks. For a description of contemporary therapy of migraine see Goodman and Gilman, "The Pharmacological Basis of Therapeutics", the fifth edition, pages 877–878 (1975).

Contemporary methods of therapy, particularly with use of ergotamine tartrate have numerous cautions, potential side effects and other unattractive features making an alternative, more reliable, regimen of therapy attractive.

DETAILED DESCRIPTION OF THE INVENTION

I have discovered, and hereby disclose, a method of treating migraine headaches using scopolamine delivered in a transdermal therapeutic system at a programmed rate of delivery. The procedure discovered is effective in treating chronic, frequent and severe migraine headaches both early at the onset of migraine or later during the course of the headache itself.

The alkaloid scopolamine or hyoscine is found chiefly in the shrub *Hyoscyamus niger* or henbane and *Scopolia carniolica*. The structure of scopolamine is known and as a naturally occurring drug is used for the treatment of many conditions, however the primary use seems to be one of treating motion sickness especially in a sustained release drug delivery system. To my knowledge scopolamine has not previously been described in the treatment of migraine headaches.

The preferred form of administering scopolamine in accordance with the method of my invention is in a transdermal therapeutic system which is designed to deliver the drug in vivo at a predetermined rate over a fixed period of time. Although sold for the prevention of nausea and vomiting the product Transderm ® Scop is commercially available in the form of a circular flat disc designed for continuous release of scopolamine following application to an area of intact skin, such as on the head, behind the ear. The flat circular disc is a multilayer laminate which when viewed from its visible surface, that is the surface attached to the skin, has 4 layers which include (1) a backing layer of alumunized, polyester film which may be skin colored; (2) a drug reservoir of scopolamine, mineral oil and polyisobutylene; (3) a microporous polypropylene membrane that controls the rate of delivery of scopolamine from the system to the skin surface; and finally (4) an adhesive formulation of mineral oil, polyisobutylene, and scopolamine. Prior to use a protective peel strip is provided covering the adhesive layer. The peel strip is removed before the circular disc is applied to the patient.

The product Transderm ® Scop is currently manufactured by ALZA Corporation of Palo Alto, Calif. and distributed by Ciba-Geigy Corporation. The supplier describes the release rate concept as including a system containing 1.5 milligrams of scopolamine which system is programmed to deliver 0.5 milligram of scopolamine at an approximately constant rate to the systemic circulation of a patient to which the patch is applied over a three-day lifetime of the system. An initial priming dose of scopolamine, which is released from the adhesive layer of the system, is provided to saturate the skin surrounding the binding sites and rapidly bring the plasma concentration of scopolamine to the required steady-state level. Continuous controlled release of scopolamine from the drug reservoir through the microporous polypropylene membrane maintains the plasma level. See "Physician's Desk Reference", 1984 edition at pages 874–875 which includes information for the patient about Transderm ® Scop and also U.S. Pat. No. 4,201,211 to Chandrasckran et al assigned to ALZA Corporation and Boehringer Ingelheim.

The method of treating migraine headaches described herein is convenient to the patient, provides relief for up to three days, has a relatively rapid onset in initial therapy and owing to its transdermal nature of drug delivery does not require the taking of oral medication which is often a problem in migraine therapy, The invention will now be further illustrated with reference to the following nonlimiting example.

EXAMPLE

The subject was a 51 year old female caucasian diagnosed as having migraine headaches for a period of some thirty-two years. Over this thirty-two year period several regimens of therapy were attempted but none of them was particularly successful in alleviating the pain and discomfort caused by recurrent migraine attacks. Attacks occurred at the rate of some 2 or 3 per month and some attacks lasted for periods of 2 or more days. In addition to an excrutiating headache the patient would experience visual distrubances, nausea, vomiting, chills and mental cloudiness.

The patient was given a supply of Transderm ® Scop circular flat adhesive disc units with instructions to apply the unit to the hairless area of the head behind one ear, the unit to remain in place for three days. At the end of three days the first unit is removed and a second unit is applied to the hairless area behind the oppposite ear to remain in place for three days. Therapy was continued at three day intervals by alternating placement of the patch.

Therapy continued for a period of 30 days during which time the patient was free of the symptoms of migraine. Several months after therapy was discontinued the patient experienced two migraine attacks, very much milder in nature than the previous attacks which subsequent attacks were controlled with Midrin (Carnrick Laboratories, Inc.), a combination of isomethepentene mucate 65 milligrams, dichloralphenazone 100 milligrams, and acetaminophen 325 milligrams. The patient reports that previous attempts at migraine therapy or prevention were largely ineffective and it was only with the use of scopolamine administered in a transdermal therapeutic system that acceptable, asymptomatic relief was obtained.

What is claimed is:

1. A method for treating migraine comprising administering to a person suffering therefrom a symptom-alleviating amount of scopolamine or a pharmaceutically acceptable salt thereof and continuing said administration until the symptoms are alleviated.

2. The method of claim 1 in which the scopolamine or a pharmaceutically acceptable salt thereof is administered transdermally at a substantially constant rate.

3. The method of claim 2 in which the scopolamine or a pharmaceutically acceptable salt thereof is delivered at a substantially constant rate to the person's systemic circulation in an amount of about 0.5 mg over a period of 72 hours.

4. A method of preventing severe migraine attack in a person susceptible to same comprising administering to said person a prophylactically effective amount of scopolamine or a pharmaceutically acceptable salt thereof and continuing said administration until susceptibility to migraine attack is diminished or is removed.

5. The method of claim 4 in which the scopolamine or a pharmeceutically acceptable salt thereof is administered transdermally at a substantially constant rate.

6. The method of claim 4 in which the scopolamine or a pharmaceutically acceptable salt thereof is delivered at a substantially constant rate to the person's systemic circulation in an amount of about 0.5 mg over a period of 72 hours.

* * * * *